US005653223A

United States Patent [19]
Pruitt

[11] Patent Number: 5,653,223
[45] Date of Patent: Aug. 5, 1997

[54] ACCURATELY CONTROLLED PORTABLE NEBULIZER

[76] Inventor: Michael D. Pruitt, 25885 Trabuco Rd., #122, Lake Forest, Calif. 92630

[21] Appl. No.: 568,946

[22] Filed: Dec. 7, 1995

Related U.S. Application Data

[63] Continuation-in-part of Ser. No. 302,203, Sep. 8, 1994, abandoned.

[51] Int. Cl.[6] .................................................. A61M 11/00

[52] U.S. Cl. ............................ 128/200.21; 128/205.24; 128/205.15

[58] Field of Search ......................... 128/200.21, 200.14, 128/200.16, 200.19, 200.22, 200.23, 202.27, 205.22, 203.12, 205.24, 203.21, 203.19, 203.24

[56] References Cited

U.S. PATENT DOCUMENTS 4,276,876 7/1981 Hakkinen .......................... 128/200.21
4,582,054 4/1986 Ferrer ................................ 128/200.23
5,533,497 7/1996 Ryder ................................ 128/200.21

*Primary Examiner*—Vincent Millin
*Assistant Examiner*—Robert N. Wieland
*Attorney, Agent, or Firm*—James G. O'Neill

[57] ABSTRACT

A hand held, single use, gas mixture discharge unit is provided for existing nebulizers to enable them to be adapted for use as a portable gas flow source for a nebulizer. The nebulizer includes an external downwardly extending base having a gas conduit extending therethrough for connection to a standard oxygen delivery tank, or to a hand held gas mixture discharge unit where it operates a valve in a controlled manner to deliver accurately metered quantities of nebulized liquid type medication to the patient, in substantially any circumstance.

20 Claims, 3 Drawing Sheets

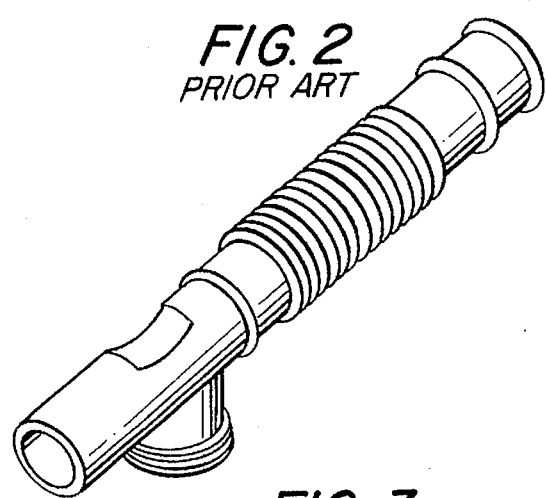
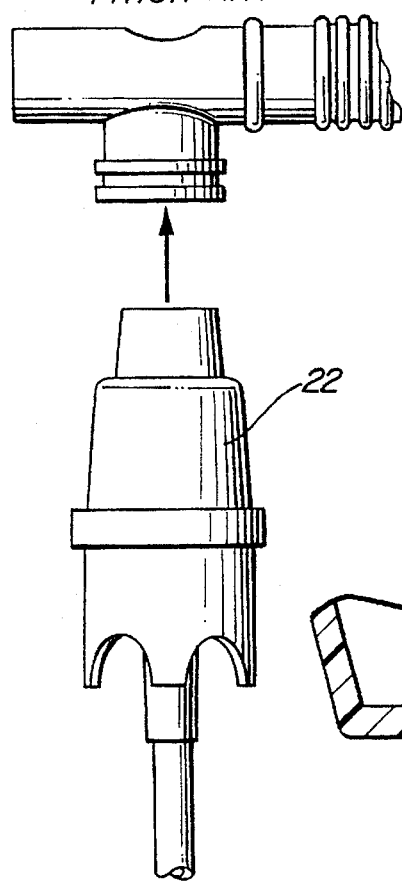
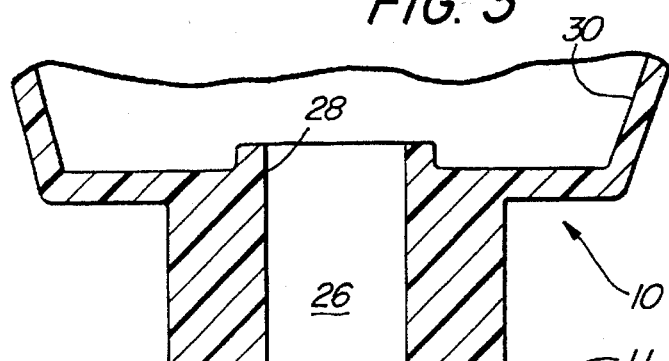
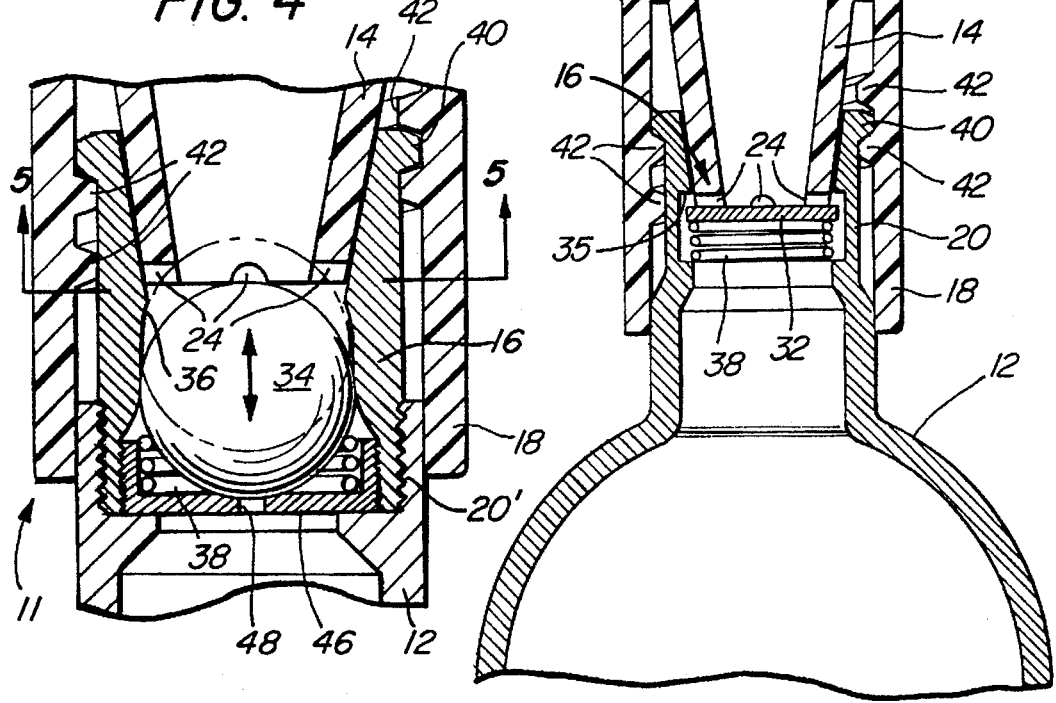

ACCURATELY CONTROLLED PORTABLE NEBULIZER

CROSS REFERENCE TO RELATED APPLICATION

This is a continuation-in-part of application Ser. No. 08/302,203, filed Sep. 8, 1994, now abandoned.

BACKGROUND OF THE INVENTION

1. Field of the Invention

This invention relates generally to nebulizers for delivering aerosolized medications for inhalation, and more particularly, for an improved portable nebulizer having a flow regulator enabling patients to deliver accurate amounts of aerosolized medications in substantially any setting.

2. Description of Related Art

Known prior art in nebulization of medications for hospital care, home care, and paramedical care consist of various systems, most of which are open and where the patient draws in medication and ambient air through a nebulizer, flex tube, T-piece and mouth piece. That is, a pneumatic device powered by a connecting tube to an air or an oxygen gas source.

The nebulizer units are commonly disposable and intended for single patient use only. They are further designed to break up liquid medication into 2 to 3 micron sized particles which are entrained in the stream of gas flow. This provides an aerosol for respiratory therapy in the treatment of chronic and/or acute pulmonary disorders or injuries.

The portability of known nebulizing devices has long been a problem and proposals have been made to make such devices more readily portable and/or adapted to be used in other circumstances.

Examples of prior art devices which attempted to provide portability to a nebulizer are shown in U.S. Pat. No. 4,257,415 to Rubin; U.S. Pat. No. 4,454,877 to Miller et al.; U.S. Pat. No. 4,582,054 to Ferrer, which relates to a portable breathing device; U.S. Pat. No. 4,949,715 to Brugger, which relates to a transportable inhalation apparatus; U.S. Pat. No. 4,955,371 to Zamba et al., which relates to a disposable inhalation activated aerosol device; U.S. Pat. No. 4,972,830 to Wong et al., which also relates to an inhalation device and method; U.S. Pat. No. 5,027,809 to Robinson, which provides an improved "peeper" for use with a known nebulizer; and U.S. Pat. No. 5,054,478 to Grychowski et al., which relates to a nebulizer for connection to a water supply, and directly to an oxygen tank.

Most of the prior art type devices are based upon Bernoulli's principle for the delivery of nebulized liquid medication. All of these standard devices require an external source of gas flow and pressure (the flow medium), in order to properly function, with the exception of the metered dose inhaler type using dry medication suspension. The prior art devices attempt to overcome the known problems of the portable gas source being bulky, heavy, cumbersome and usually requiring a stand with wheels, or some other type of transporting feature, such as a shoulder strap, because the portable gas sources weigh in at as much as fifteen pounds, or even more. And, although some of the above cited prior art devices overcame some of the problems with the known portable gas sources, they do not meet all the perceived and real needs of some of the more severely impaired patients, and do not meet today's need of accurate delivery of medication in substantially any setting.

All of the devices in the prior art use source gas units to drive or operate these devices, and are almost always interconnected by a length of tubing known as a standard oxygen tubing, and not by direct means. These known prior art devices require various types of adapters and/or connection means to secure or fix the interconnecting tubing between the source and the device before operation and delivery of medication will occur. However, these adapters are usually of a conical friction type fit and must be pressed into the tubing by hand, or threaded into a flow control device which is then attached to the source unit. Furthermore, they are usually constructed so that inadvertent disconnection or disruption can occur anywhere along the route of connection, thus interrupting the delivery of medication.

In today's hospital environment, many patients, after an acute medical event and intervention or diagnosis of a chronic condition, are prescribed supplemental oxygen flow for home use during recovery and/or rehabilitation. Because oxygen is now deemed a drug and its use monitored, physicians must write an order or prescription, before it is made available to the patient. Furthermore, standard hospital patient release protocols limit the amount of oxygen allowed for home use, to liter flows of less than four liters per minute (lpm), to avoid any inadvertent oxygen toxicity, with specific diagnosis being the only exception.

Prior and known specifications also expose the fact that to nebulize the most advantageous particle size for inhalation (2 to 3 microns in diameter), a sufficient source of gas flow, i.e., between 5 to 7 lpm must be available either from a large cylinder source, or a generation device such as a compressor, or the like, to enable known nebulizers to properly function.

Since most home use oxygen is supplied by low flow generating devices such as concentrators, compressors and the like, rather than large cylinders enabling high flows up to 15 lpm, these low flow home generating devices are limited to maximum flow capabilities of 4 lpm. Nevertheless, patients have to power their treatment devices via these modalities, thereby receiving a much less than optimum personally administered treatment.

Some patients are able to use metered dose inhalers (MDI), in that they have the inspiratory capacity/neuromotor-function to benefit from this type of device, and its pocket size availability. However, many more patients, because of physical impairments and/or lack of abilities, do not possess the necessary inspiratory capacity to be able to use known MDI devices. These patients, therefore, must be tethered to a source device in the home or elsewhere. Such source devices usually require electricity. Such devices diminish the mobility, recovery and rehabilitation of such patients, and do not always provide the necessary medical treatment regiment prescribed by the doctor. Still other devices require mandatory return to home or other places, such as clinics or hospitals, so that the patients may receive their next scheduled nebulized liquid treatment.

The portable nebulizer of the present invention overcomes many of the problems of the prior art devices by providing an easy to use and operate hand held device which provides accurately controlled nebulizer flow rates for a given patient, using known nebulizers, in substantially any setting.

SUMMARY OF THE INVENTION

Accordingly, it is a general object of the present invention to provide an improved portable nebulizer device. It is a more particular object of the present invention to provide an improved nebulizer device having a quick disconnect conduit coupling feature between the nebulizer and a source of pressurized gas. It is a further particular object of the present invention to provide an improved portable nebulizer device utilizing a small compact, hand held pressurized gas unit connected to a known type nebulizer and including unique valve means therein for accurate control. It is yet another particular object of the present invention to provide an improved portable nebulizer device which may be adapted to be used with available oxygen, high flow, or low flow type devices in almost any setting. It is still a further particular object of the present invention to provide an improved portable nebulizer device having a small, portable, hand held, gas source easily adapted to be connected to and from a nebulizer device, for accurate control of nebulized liquids.

In accordance with one aspect of the present invention there is provided a standard type nebulizer for inhalation of nebulized fluid by a patient. This nebulizer includes an extending portion which cooperates with and opens and closes a valving means in a reduced diameter neck portion of a small, hand held, gas source to enable accurately controlled gas flow into the nebulizer so as to provide enhanced nebulization of the desired liquid to be inhaled and thus provide better flow of medication to a patient in substantially any situation or setting. The nebulizer also includes an adapter for use with known large high flow or low flow oxygen type tanks for home, clinic or hospital use. The valve includes a regulator means for even more accurate flow rates.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, in which:

FIG. 1 is a partial front elevational view of a prior art T-section, reservoir and nebulizer device;

FIG. 2 is a further perspective view of the prior art T-section and reservoir of FIG. 1;

FIG. 3 is an enlarged partial cross-sectional view of an improved nebulizer base connected to a hand held gas source having a disc-type flow control valve means therein, of the present invention;

FIG. 4 is a further enlarged partial cross-sectional view showing a further embodiment of a flow control valve means of the ball type, and including a regulating means removably mounted in a neck portion of a hand held gas source;

DESCRIPTION OF THE PREFERRED EMBODIMENTS

Figure 5:
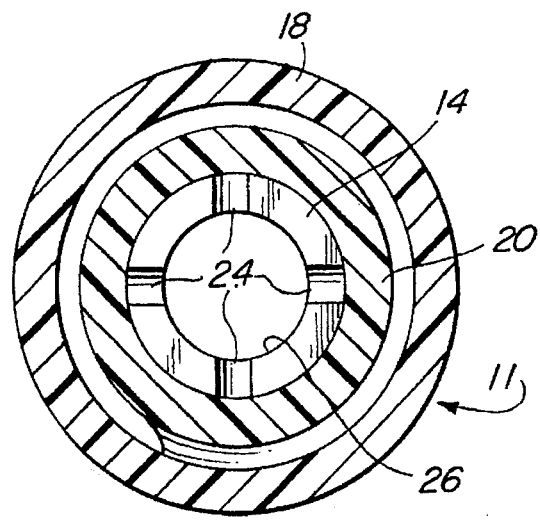
FIG. 5 is a cross sectional view taken along line 5—5 of FIG. 4.
Figure 6:
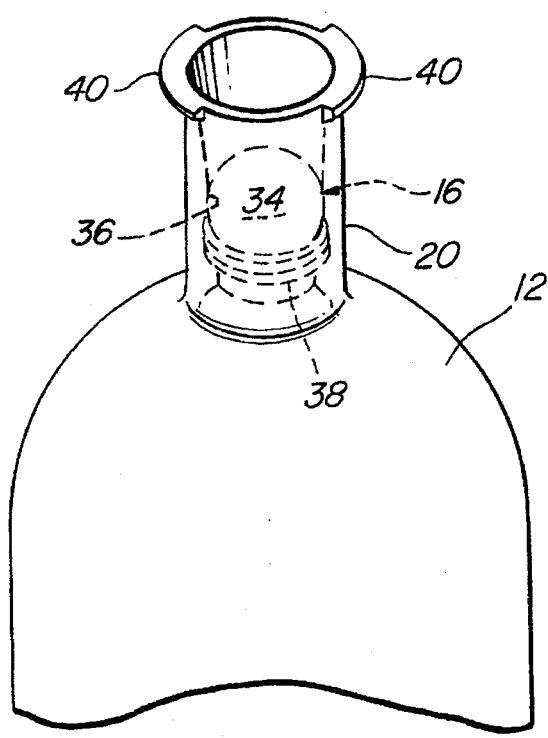
FIG. 6 is an enlarged partial perspective view of a hand held gas source showing a hand held portable gas source having a ball type valve means within an integral neck portion thereof.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide for an improved combination portable nebulizer and portable gas source means. The improved nebulizer of the present invention is generally identified at 10, and generally includes an upper reservoir of any desired configuration known to those skilled in the art, having an improved and novel lower or downwardly extending base portion 11, with an outer sleeve 18, which may be substantially cylindrical, or which may include one or more openings therein, for connection to a hand held, portable gas source or cylinder 12, which is preferably of the high pressure, high flow rate type holding a predetermined amount of gas. The downwardly extending base portion 11 includes a substantially conical inner lumen or sleeve means 14, which cooperates with and operates a valve means 16 mounted to, and held within a neck portion 20 of the high flow rate, hand held gas source 12. The neck portion 20 is preferably formed integrally with, but may be removably mounted to the gas source 12. The gas source 12 is preferably cylindrically shaped, approximately 5" long and 1 and ½" in diameter and holds approximately 66 to 88 liters of compressed gas under a predetermined amount of pressure, to provide the desired flow rates through the valve means 16, and any regulator means used, so as to be accurately delivered to the patient, using the present invention.

The valve means 16 is designed to allow reuse of the gas source 12 by recharging the same through the reduced diameter neck portion 20, in a manner known to those skilled in the art.

The reservoir or top portion of the nebulizer 10 would be substantially the same as known nebulizers, such as nebulizer 22 shown in prior art FIG. 1. The main differences occurring in the shape and size of base 11 having the downwardly extending sleeve 18 and inner, substantially conically shaped lumen or sleeve 14. That is, in operation, when pressurized gas is released from the gas source 12, it travels upwardly and is accurately controlled via the regulating means and valve means 16, as described in more detail below, and then passes through a plurality of openings, or the like, 24 on or through the downwardly extending conical inner lumen or sleeve 14. The pressurized gas will then flow upwardly through a conduit 26 and through an increased diameter opening 28, into a reservoir area 30 where the fluid to be nebulized is held.

The valve means 16 may take any desired shape, and may be mounted in the neck portion 20, 20' in any known manner, either in pieces or as a single unit, as by being screw threaded therein. However, the valve means 16 is presently preferably formed to include a control valve, such as disk type element 32 shown in FIG. 3, or a ball type element 34, as shown in FIG. 4. The disk element 32 and ball element 34 are normally biased upwardly against annular valve seats 35, 36, respectively formed in the valve means 16, by a biasing means 38, such as a spring.

Depending on the pressure of the compressed gas in the gas cylinder 12, the flow of pressurized gas therefrom may require flow control or regulator means to accurately control the flow rate. A presently preferred means for such flow control is shown in FIG. 4. The interior diameter of an integral neck portion 20, or a shorter portion 20' having a removable valve means 16, is provided with a stepped internal diameter, and cup type means 46 is secured in valve means 16 or neck portion 20, 20', as shown in FIGS. 4 and 8, as, for example, by being threadedly inserted therein. This cup means 46, may be made from any available metallic material, but is preferably formed from brass, and acts in a dual capacity. First to form a lower surface against which biasing spring 38 may sit. And, secondly as a regulating means, due to a restricted central opening or orifice 48 formed therethrough. This opening or orifice may vary depending on the pressure of the gas in the gas cylinder 12, but is always sized and dimensioned so as to provide extremely accurate flow of pressurized gas from gas cylinder 12 into valve means 16. In order that the cup means 46 may be easily removed and cleaned or replaced, the cup means is preferably threadedly secured within the interior of the neck portion 20, 20' of the gas source 12 used, or in the valve means 16.

Figure 8:
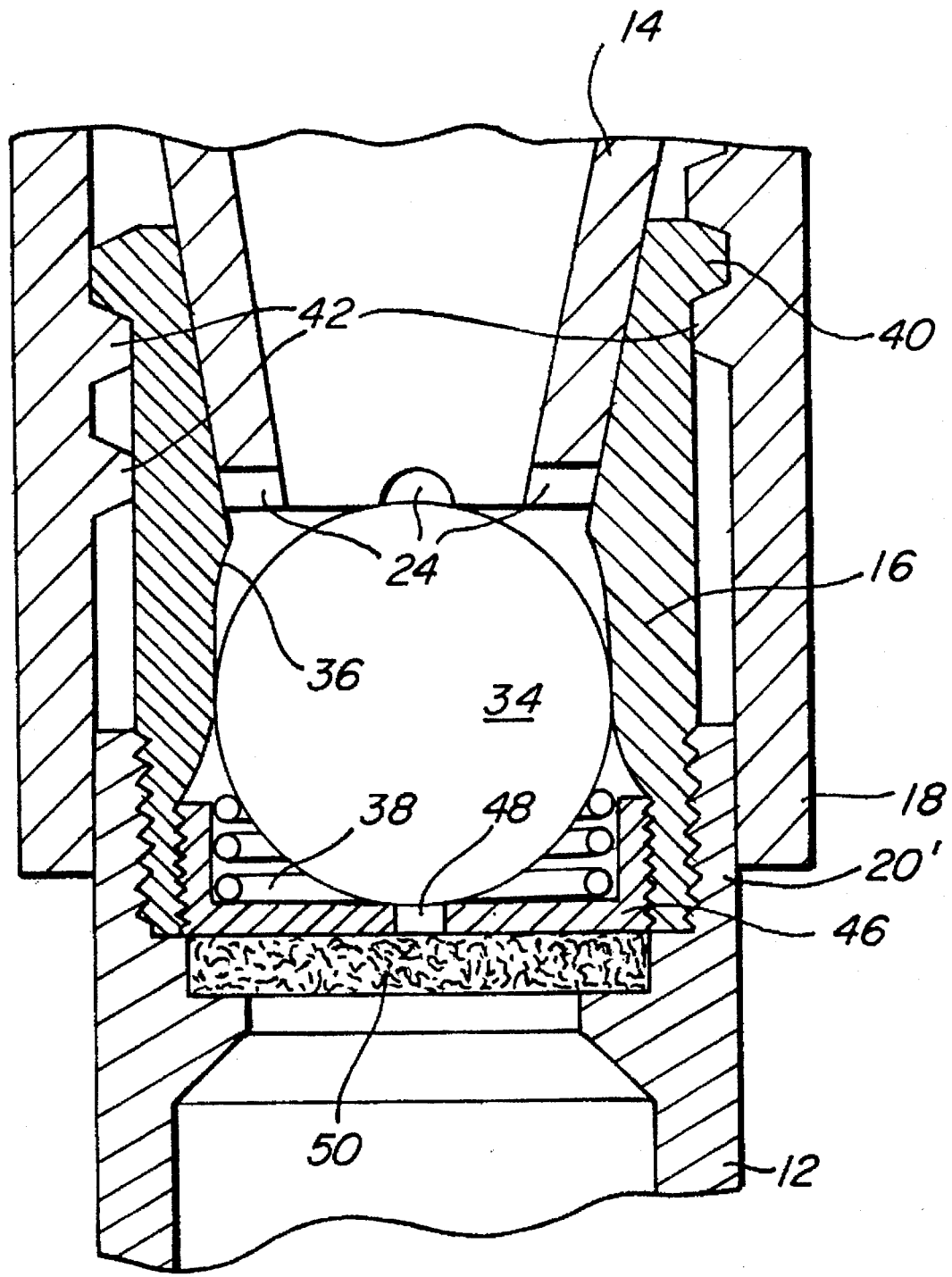
FIG. 8 is a further enlarged partial cross-sectional view showing a further embodiment of a ball type valve means with a plurality of regulator means upstream thereof.

Turning now to FIG. 8, there shown is a further enlarged sectional view of a valve means 16 having a ball type valve 34, biased against an annular valve seat 36, and a cup means 46 having a restricted orifice 48 therein. Additionally, to still further accurately control the flow of gas, upstream of the valve means 16, from gas cylinder 12, a second gas flow control or regulator means 50, such as a wafer formed from an aggregate of compressed beads of a poly or brass, may be provided to limit gas permeability through orifice 48, based on Poiseuille's principal, beginning at 7 to 8 liters per minute. With the wafer 50 placed upstream of the cup means 46, before the orifice 48, flow of gas to the valve means 16 will be restricted, so as to more accurately control the flow of gas from the gas cylinder 12.

As can be seen in FIG. 3, in operation, when the base 11 of the nebulizer 10 is pressed down into the neck portion 20 of the gas source 12, as by turning either or both the nebulizer 10 and gas source 12, one half a turn with respect to each other, that the lowest or end portion of inner conical sleeve 14 will contact the valve means 16, as by moving the disk element 32, or ball type valve 34 (FIG. 4), away from its respective annular valve seat 35 or 36, against the biasing means 38, so as to allow flow of pressurized gas, from the gas source 12, through one or more regulators or restrictors 48, 50 and through the valve seat 35 or 36, and then through openings 24, and upwardly through conduit 26, into the nebulizing portion of the device.

As can be best seen in FIGS. 3, 4, 6 and 8, the top or upper portion of the valve means 16 includes an enlarged rim or the like 40, which preferably is only formed partially around the circumference thereof, and which is quickly inserted into, rotated and captured within screw threads 42, formed interiorly of the base 11 of the nebulizer device 10, on the interior surface of downwardly extending outer sleeve 18. Since the nebulizer device is preferably made from a resilient material, such as plastic or the like, when the gas cylinder 12 and the base 11 of nebulizer 10 are screwed together, preferably in an exact one-half turn movement of either or both of the gas cylinder and nebulizer, the downwardly extending lumen or sleeve 18 will capture and securely hold rim 40 in the threads 42, thus securing the nebulizer to the gas source. The screw threads 42 and rim 40, as well as where the valve means 16 is mounted within the neck 20, are accurately sized and dimensioned so that the base 11 of the nebulizer and neck 20 of the gas source 12 fit together to allow an exact one-half turn movement in the selected direction to sealingly bring the base of the nebulizer and gas source together, and open the valve means 16, a predetermined distance, to thereby allow an accurate flow of a predetermined amount of gas from the gas source, through the neck 20 and into the nebulizer. Furthermore, the base 11 of the nebulizer and neck 20 of the gas source 12 are also easily separated by a similar one-half rotation, in the opposite direction.

Figure 7:
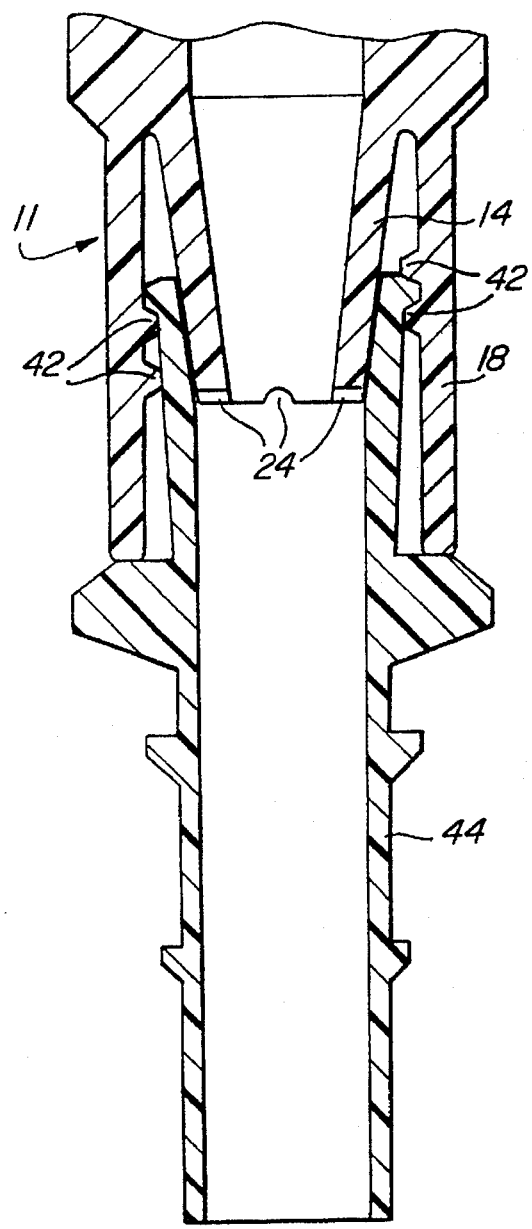
FIG. 7 is an enlarged partial sectional view of the connecting base portion of the improved nebulizer of the present invention, with the hand held portable gas source removed and an adapter threadedly mounted therein for securing to known, standard oxygen tubing from high flow oxygen and/or gas type sources.

Turning now to FIG. 7, the base 11 of nebulizer 10 is shown having an adapter 44 inserted and secured therein much in the same manner as the top reduced portion 20 of the gas cylinder 12 may be inserted therein. However, the adapter 44 includes a downwardly extending cylindrical portion adapted to be attached to a standard oxygen tubing (not shown), so that the nebulizer 10 may be connected to a high flow or other, non-portable gas or oxygen source, used in a hospital, an out patient area, and/or a home.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An aerosol generating nebulizer including a downwardly extending base connected to a small, cylindrical, portable, hand held gas source, comprising, in combination:

a pair of circular sleeve members formed integrally with said downwardly extending base;

a first of said pair of sleeve members being an outer sleeve and a second of said pair of sleeve members being a conical inner sleeve having a hollow conduit extending therethrough into said nebulizer;

said small, cylindrical, portable, hand held gas source being connected to said first of said pair of sleeve members and said second of said pair of sleeve members; and regulator means and biased valve means held within said small, cylindrical, portable, hand held gas source in a neck portion thereof, said valve means being opened when contacted by said conical inner sleeve against the action of a biasing means to accurately control the flow of pressurized gas from said small, cylindrical, portable, hand held gas source, through said neck portion, around said valve means and into said hollow conduit.

2. The combination nebulizer and gas source of claim 1 wherein said conical inner sleeve includes a base which mechanically contacts said valve means, and a plurality of openings are formed in said base, to allow gas flow therethrough and into said hollow conduit.

3. The combination nebulizer and gas source of claim 2 wherein said valve means is comprised of a disk valve biased against a valve seat formed within said neck portion of said small, cylindrical, portable, hand held gas source.

4. The combination nebulizer and gas source of claim 3, further including biasing means normally biasing said valve disk in a direction toward said valve seat to prevent gas flow therethrough.

5. The combination nebulizer and gas source of claim 2 wherein said valve means is a ball type element cooperating with a valve seat formed internally of said neck portion of said small, cylindrical, portable, hand held gas source.

6. The combination nebulizer and gas source of claim 5 wherein said regulator means is a cup means having an orifice therein mounted upstream of said valve means in said neck portion of said small, cylindrical, portable, hand held gas source and restricting gas flow from said small, cylindrical, portable, hand held gas source to said valve means.

7. The combination nebulizer and gas source of claim 5 wherein there are at least two regulator means mounted upstream of said valve means in said neck portion of said small, cylindrical, portable, hand held gas source.

8. The combination nebulizer and gas source of claim 7 wherein a first of said at least two regulator means is a compressed aggregate wafer, and a second of said at least two regulator means is a cup means having a restricted orifice formed therein.

9. The combination nebulizer and gas source of claim 8 wherein said compressed aggregate wafer is made from a material selected from brass or poly beads.

10. The combination nebulizer and gas source of claim 8 wherein said cup means is threadedly mounted in said neck portion of said small, cylindrical, portable, hand held gas source, upstream of said valve means, away from said nebulizer.

11. The combination of an aerosol generating nebulizer having a downwardly extending base and a small, cylindrical, portable, hand held gas source, comprising;

said base having an external sleeve having at least one opening therein and formed from a resilient material and receiving a rim formed on an open end of a neck portion of said small, cylindrical, portable, hand held gas source therein between an inner surface of said external sleeve and an outer surface of an inner conical sleeve; and said inner conical sleeve having a hollow central conduit, an outer end, and a plurality of openings formed therein; said outer end contacting a valve means held within said neck portion of said small, cylindrical, portable, hand held gas source, and moving said valve means against a biasing means, to control flow of pressurized gas held within said small, cylindrical, portable, hand held gas source through a regulator means, through said neck portion, around said valve means, through said openings in said outer end of said conical inner sleeve, and into said hollow control conduit to said nebulizer.

12. The combination nebulizer and gas source of claim 11 wherein said valve means is a disk element normally biased against a valve seat formed within said neck portion of said small, cylindrical, portable, hand held gas source; said disk being moved and depressed against said biasing means by the thrust of said outer end of said conical inner sleeve when pressed against said disk, as said nebulizer and said small, cylindrical, portable, hand held gas source are threadedly coupled.

13. The combination nebulizer and gas source of claim 11 wherein said valve means is a ball type valve element normally biased against a valve seat formed in said neck portion of said small, cylindrical, portable, hand held gas source, and wherein said biasing means is a spring normally biasing said ball type valve element into contact with said valve seat to prevent flow of gas from said small, cylindrical, portable, hand held gas source.

14. The combination nebulizer and gas source of claim 13 wherein said regulator means is held in said neck portion of said small, cylindrical, portable, hand held, gas source.

15. The combination nebulizer and gas source of claim 14 wherein there are two regulator means, a first of said two regulator means being a compressed aggregate wafer, and a second of said two regulator means being a cup means having a restricted orifice formed therein.

16. The combination nebulizer and gas source of claim 15 wherein said compressed aggregate wafer is made from a material selected from brass or poly beads.

17. The combination nebulizer and gas source of claim 16 wherein said cup means is threadedly mounted in said neck portion of said small, cylindrical, portable, hand held gas source, upstream of said valve means, away from said nebulizer.

18. An aerosol generating nebulizer connected to a small, cylindrical, portable, hand held gas source, comprising;

a base formed on said nebulizer, said base having an external sleeve having at least one opening therein and formed from a resilient material and receiving a rim formed on a neck portion of said small, cylindrical, portable, hand held gas source in an internal screw thread formed between an inner surface of said external sleeve and an outer surface of an inner conical sleeve, formed on said base;

said inner conical sleeve having an outer end with a plurality of openings formed therein;

a valve means inserted in said neck portion, and normally biased against a valve seat; biasing means holding said valve means against said valve seat until contacted by said outer end of said conical inner sleeve, whereby said valve means is moved away from said valve seat, a predetermined amount, when said rim of said small, cylindrical, portable, hand held gas source is rotated within said internal screw thread between said external sleeve and said inner conical sleeve; and a plurality of regulator means mounted in said neck portion of said small, cylindrical, portable, hand held gas source to restrict the flow of gas reaching said valve means.

19. The combination nebulizer and gas source of claim 18 wherein a first of said plurality of regulator means is a compressed aggregate wafer, made from a material selected from brass or poly beads, and a second of said plurality of regulator means is a cup means, removably mounted in said neck portion and having a restricted orifice formed therein.

20. The combination nebulizer and gas source of claim 18 wherein said valve means is a ball type valve normally biased against said valve seat to prevent the flow of gas therethrough by a spring means held between said cup means and said ball type valve.

* * * * *